(12) United States Patent
Baert et al.

(10) Patent No.: US 9,943,035 B2
(45) Date of Patent: Apr. 17, 2018

(54) COMBINE HARVESTER CLEANING SYSTEM DRIVE ASSEMBLY

(71) Applicant: CNH Industrial America LLC, New Holland, PA (US)

(72) Inventors: Matthias Baert, Varsenare (BE); Tom De Smet, Maldegem (BE); Frederik Tallir, Esen (BE); Bart M. A. Missotten, Herent (BE)

(73) Assignee: CNH Industrial America LLC, New Holland, PA (US)

( * ) Notice: Subject to any disclaimer, the term of this patent is extended or adjusted under 35 U.S.C. 154(b) by 206 days.

(21) Appl. No.: 14/724,312

(22) Filed: May 28, 2015

(65) Prior Publication Data

US 2016/0345501 A1 Dec. 1, 2016

(30) Foreign Application Priority Data

May 28, 2015 (BE) .................. 2014/0408

(51) Int. Cl.
| | |
|---|---|
| *A01F 12/56* | (2006.01) |
| *A01F 12/44* | (2006.01) |
| *A01D 75/28* | (2006.01) |
| *A01D 41/127* | (2006.01) |

(52) U.S. Cl.
CPC .......... *A01F 12/56* (2013.01); *A01D 41/1276* (2013.01); *A01D 75/282* (2013.01); *A01F 12/446* (2013.01); *A01F 12/448* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,461,314 | A | * | 7/1923 | Jones ................ A01F 12/38 460/85 |
| 3,049,128 | A | * | 8/1962 | Hing ................. A01F 12/30 460/85 |
| 4,455,812 | A | | 6/1984 | James |
| 4,466,230 | A | | 8/1984 | Osselaere et al. |
| 6,412,260 | B1 | | 7/2002 | Lukac et al. |
| 7,059,982 | B2 | | 6/2006 | Jonckheere et al. |
| 8,626,400 | B2 | | 1/2014 | Sheidler et al. |

(Continued)

FOREIGN PATENT DOCUMENTS

| | | |
|---|---|---|
| DE | 29903969 U1 | 6/1999 |
| EP | 2510777 A1 | 10/2012 |
| WO | WO 2014106633 A1 * 7/2014 | ............ A01F 12/38 |

*Primary Examiner* — Alicia Torres
(74) *Attorney, Agent, or Firm* — Peter K. Zacharias; Patrick M. Sheldrake

(57) ABSTRACT

A combine harvester having a cleaning system with at least one cleaner assembly for cleaning the harvested and a drive assembly connected to the cleaning system to drive the cleaning system, thereby driving the at least one cleaner assembly to perform a reciprocating cleaner movement. The drive assembly comprises a variable speed drive assembly with a rotary drive comprising a rotatable output shaft for driving the cleaning system, a transmission to connect the rotatable output shaft to the at least one cleaner assembly, the transmission configured to convert an angular movement of the rotatable output shaft to the reciprocating cleaner movement, and a control unit to control an angular velocity of the rotatable output shaft based on an input signal.

11 Claims, 2 Drawing Sheets

(56) References Cited

U.S. PATENT DOCUMENTS

| | | | | |
|---|---|---|---|---|
| 2003/0186731 A1* | 10/2003 | Voss | A01F 12/448 | 460/101 |
| 2005/0282601 A1* | 12/2005 | Duquesne | A01F 12/448 | 460/101 |
| 2012/0184339 A1* | 7/2012 | Schulz | A01F 12/444 | 460/78 |
| 2015/0080070 A1* | 3/2015 | Johnson | A01F 12/448 | 460/5 |

* cited by examiner

COMBINE HARVESTER CLEANING SYSTEM DRIVE ASSEMBLY

This application claims priority to Belgium Application BE2014/0408 filed May 28, 2014, which is incorporated herein by reference in its entirety.

FIELD OF THE INVENTION

The invention relates to the field of combine harvesters and more specifically to operating a cleaning system as applied in such a combine harvester.

BACKGROUND OF THE INVENTION

The invention pertains to a combine harvester having a cleaning system for separating harvested seeds from by-products that are harvested along with said seeds.

Combine harvesters are widely used in the harvesting of various types of crop such as grain, corn of which the seed is harvested. Typically, a combine harvester comprises a header e.g. having a cutter bar, which cuts the plants that contain the seeds to be harvested from the field. The combine harvester may further include a threshing system, provided inside the harvester, for threshing the harvested crop, whereby the seeds are separated from the other parts of the plants. The stalks of the harvested plants are removed from the combine harvester via a straw walker and a mixture of harvested seeds and by-products remains in the combine harvester. These by-products (e.g. chaff or "ears") are generally smaller than the stalks that are removed from the combine harvester via the straw walker.

The mixture of harvested seeds and these by-products as outputted by the threshing system is typically provided to a cleaning system, in which the threshed seeds are separated from the by-products. The cleaning system generally comprises one or more grain pans and one or more sieves, which perform a reciprocating movement during use. The sieved seeds are then collected and transported to the grain tank of the combine harvester, which is generally emptied periodically.

The grain pan and sieve or sieves of the cleaning system are generally arranged at an angle relative to the horizontal, with the front end of the sieve (that is, the end closest to the cutter bar) lower than the rear end of the sieve. The reciprocating movement of the grain pan and sieve makes that the seeds and by-products are thrown upwards and backwards by the grain pan or sieve, respectively. A fan blows air over and through the sieve, to catch the lighter particles of the by-products and keep them airborne until they are blown out of the combine harvester.

In known arrangements, the combine harvester comprises a drive mechanism for the cleaning system. Such a drive mechanism typically comprises a rotatable drive shaft, that drives the grain pan or grain pans as well as the sieve or sieves. The grain pans and sieves are connected to the rotatable drive shaft through a transmission comprising mechanical elements such as eccentric drives and linkages.

It has been observed that the effectiveness or yield of the cleaning process may vary substantially, depending on the operating conditions of the harvester.

It is therefore an object of the present invention to provide in an improved cleaning system for a combine harvester.

SUMMARY OF THE INVENTION

It would be desirable to provide a combine harvester having a cleaning system with a yield or throughput that is less affected by the operating conditions of the harvester.

To address this concern, in an aspect of the invention a combine harvester is provided, the combine harvester comprising:
- a cleaning system configured to receive a flow of harvested and threshed crop, the cleaning system comprising at least one cleaner assembly to clean the harvested and threshed crop;
- a drive assembly connected to the cleaning system, the drive assembly being configured to drive the cleaning system, thereby driving the at least one cleaner assembly to perform a reciprocating cleaner movement, wherein
the drive assembly comprises a variable speed drive assembly, the variable speed drive assembly comprising:
  - a rotary drive comprising a rotatable output shaft for driving the cleaning system;
  - a transmission configured to connect the rotatable output shaft to the at least one cleaner assembly of the cleaning system; the transmission being configured to convert an angular movement of the rotatable output shaft to the reciprocating cleaner movement; and
  - a control unit configured to control an angular velocity of the rotatable output shaft based on an input signal received at an input terminal of the control unit.

The combine harvester according to the present invention comprises a cleaning system for cleaning a flow of harvested and threshed crop. Typically, such a cleaning system comprises one or more cleaner assemblies.

Within the meaning of the present invention, a cleaner assembly can be a sieve assembly or a grain pan assembly. A sieve assembly can comprise one or more sieves. A grain pan assembly can comprise one or more grain pans.

In order to clean the harvested and threshed crop (i.e. a mixture of harvested seeds and by-products such as chaff or "ears"), the harvested and threshed crop is submitted to a reciprocating movement of the cleaner assembly. The reciprocating movement of the grain pan or sieve of the cleaner assembly enables the seeds and by-products to propagate along the sieve, thereby, in case of a sieve, separating the seeds (which pass throught apertures of the sieve) and the by-products. Typically, such a reciprocating sieve movement can be described as a linear, curved, circular or elliptical movement comprising a first portion whereby the sieve is moved forwards, i.e. towards the front end of the sieve (typically combined with a downward movement) and a second portion whereby the sieve is moved backwards (typically combined with an upward movement). Such a movement enables the flow of harvested and threshed crop which is supplied to a front end of the sieve, to be moved or propagated from the front end of the sieve to the back end.

During such movement of the sieve, the flow of seeds and by-products propagates over the sieve, and, due to a difference in weight or size of the different components, a separation of the components (e.g. the separation of grain) can be realized.

In an embodiment, the combine harvester comprises a fan configured to blow air over and through the sieve, to catch the lighter particles of the by-products and keep them airborne until they are blown out of the combine harvester.

In order to provide in the reciprocating cleaner movement, the combine harvester according to the present invention comprises a drive assembly connected to the cleaning system. In accordance with the present invention, the drive assembly comprises a variable speed drive assembly. In known combine harvesters, the drive assembly for driving the cleaning system operates at a substantially constant speed, irrespective of the operating conditions of the harvester. Typically, a combine harvester comprises a central drive having a shaft (also referred to as the input shaft) operating at a speed that is proportional to the speed of the engine of the harvester, said speed being substantially constant during operation, i.e. during the harvesting process. In such arrangement, different output shafts may be driven by the central drive, e.g. by means of belt transmissions, to operate various systems of the combine harvester, such as the cleaning system or a threshing system or one or more augers to transport clean grain towards an on-board grain tank. Typically, the various systems used for cleaning and transporting the harvested crop are thus driven by the same central drive at a substantially constant speed.

In accordance with the present invention however, it is proposed to apply a variable speed drive for driving the cleaning system, in particular for driving the one or more cleaners of the cleaning system. In order to drive the one or more cleaners of the cleaning system at a variable speed, the combine harvester according to the present invention comprises a variable speed drive assembly, the variable speed drive assembly comprising:

a rotary drive comprising a rotatable output shaft for driving the cleaning system; and a transmission configured to connect the rotatable output shaft to the at least one cleaner assembly of the cleaning system; the transmission being configured to convert an angular movement of the rotatable output shaft to the reciprocating cleaner movement;

In accordance with the present invention, the variable speed drive assembly comprises a rotary drive and a transmission for converting an angular movement of the rotatable output shaft of the rotary drive to the reciprocating cleaner movement.

In accordance with the present invention, the angular speed of the output shaft can be controlled, i.e. adjusted.

Rendering the angular speed of the output shaft of the rotary drive adjustable can be realized in various ways.

In an embodiment, the rotary drive may e.g. be a dedicated variable speed drive for driving the cleaning system. In order to adjust the angular velocity of an output shaft of such a drive, a variator, a gear box or a variable transmission such as a CVT (continuous variable transmission) or IVT (infinitely variable transmission) may be applied.

In an embodiment, a rotatable output shaft having a variable angular velocity may be obtained by considering a rotary drive (such as the aforementioned central drive) comprising a rotatable input shaft having a constant speed, combined with a variable transmission between the rotatable input shaft and the rotatable output shaft, i.e. connecting the rotatable input shaft and the rotatable output shaft. Examples of such variable transmissions include a variator or a CVT (continuous variable transmission) or IVT (infinitely variable transmission).

In accordance with the present invention, the combine harvester further comprises a control unit configured to control an angular velocity of the rotatable output shaft based on an input signal received at an input terminal of the control unit. Such a control unit may e.g. include a microcontroller or microprocessor or the like. Such control unit may either control the angular velocity of the output shaft of the rotary drive (in case the rotary drive e.g. includes an electromotor as rotary drive) directly or control a gear ratio of a variable transmission to control the angular velocity. In accordance with the present invention, the control unit comprises an input terminal for receiving an input signal.

Such input signal may e.g. be generated by a user interface available in a cabin of the combine harvester, enabling an operator of the harvester to provide the input signal to the control unit.

Alternatively, the input signal for the control unit may be based on a sensor signal.

As an example, the combine harvester according to the present invention may comprise a sensor for sensing an inclination of the combine harvester, the sensor being configured to provide a signal representative of the inclination as an input signal to the control unit.

Within the meaning of the present invention, the inclination of the combine harvester is considered positive (i.e. at a positive angle) when the harvester drives uphill and is considered negative (i.e. at a negative angle) when the harvester drives downhill.

The combine harvester according to the present invention enables to adjust an operating speed of the cleaning system based on operating conditions of the harvester. In a particular embodiment, the operating speed of the cleaning system (which depends on the angular speed of the output shaft of the rotary drive) can be adjusted based on an inclination of the harvester. It has been devised by the inventors that the effectiveness of the cleaning system, i.e. the effectiveness of the separation process of seeds and by-products, may depend on the operating conditions of the harvester, in particular the inclination of the harvester. It has e.g. been noticed that, in case the combine harvester moves up-hill, the flow of seeds and by-products that need to be separated may propagate too fast towards the end of the sieve, thereby adversely affecting the yield of the separation process Similarly, in case the combine harvester moves down-hill, the flow of seeds and by-products that need to be separated may propagate too slow towards the end of the sieve. As a result, a varying capacity (i.e. the amount of harvested and threshed crop processed by the cleaning system per unit of time) may be noticed. Such a varying capacity may adversely affect the removal and transport of the clean grain towards an on-board grain tank by a transport system (e.g. an auger based transport system), because this transport system is typically dimensioned to handle a particular capacity.

By means of the variable speed drive system as applied in the combine harvester according to the present invention, the operating speed of the cleaning system can be adjusted such that the capacity of the cleaning system may remain substantially constant. In case the combine harvester moves up-hill, the control unit of the combine harvester according to the present invention may e.g. reduce the operating speed (i.e. the speed associated with the reciprocating cleaner movement), in order to maintain the cleaning capacity at or near the nominal capacity. Similarly, In case the combine harvester moves down-hill, the control unit of the combine harvester according to the present invention may e.g. increase the operating speed, in order to maintain the cleaning capacity at or near the nominal capacity.

As such, in an embodiment, the control unit may be configured to control the angular velocity of the rotatable output shaft inversely proportional to the inclination.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
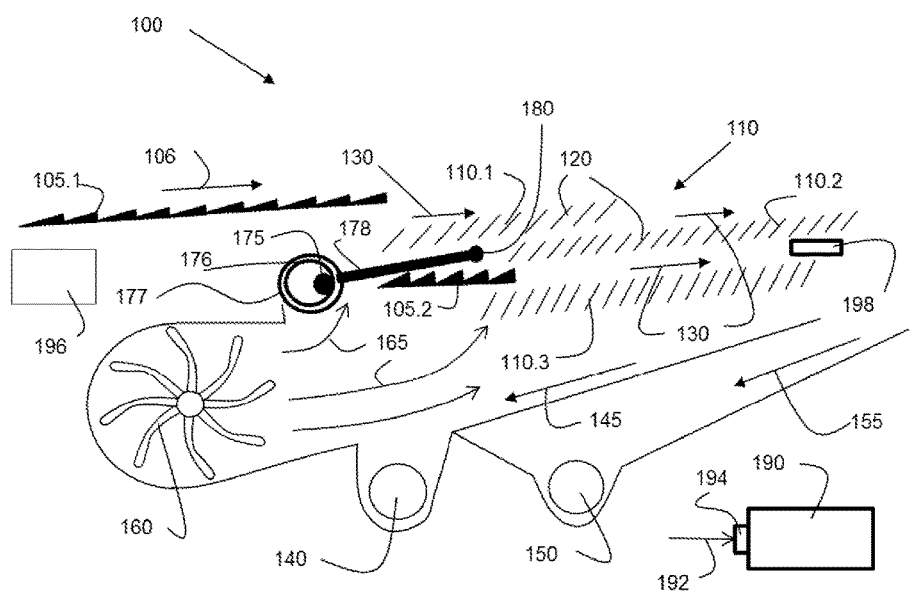
FIG. 1 depicts a cleaning system as can be applied in a combine harvester according to the present invention.

FIG. 1 depicts a cleaning system 100 as can be applied in a combine harvester according to the present invention.

The cleaning system 100 as schematically shown comprises a pair of grain pans (105.1, 105.2) configured to receive a flow of harvested and threshed crop and transport the flow of crop (indicated by the arrow 106) towards a sieve assembly 110 of the cleaning system 100.

Typically, a combine harvester comprises a header e.g. having a cutter bar, which cuts the plants that contain the seeds to be harvested from the field. The harvested crop may subsequently be processed in a threshing system, provided inside the harvester, for threshing the harvested crop, whereby the seeds are separated from the other parts of the plants. By means of such threshing system, the stalks of the harvested plants can removed from the combine harvester via a straw walker and a mixture of harvested seeds and by-products remains. The mixture of harvested seeds and these by-products as outputted by the threshing system is typically provided to a cleaning system such as cleaning system 100, in which the threshed seeds are separated from the by-products.

In accordance with the present invention, the cleaning system 100 comprises one or more cleaner assemblies, whereby the feature 'cleaner assembly' may refer to an assembly including one or more sieves or grain pans or a combination thereof.

The grain pans 105.1 and 105.2 as schematically shown may e.g. be a conveyer or auger-type of transport system or a plate-like structure undergoing a circular or elliptical movement to transport the received flow of crop in the indicated direction 106. The cleaning system 100 further comprises a sieve assembly 110 comprising three sieves 110.1, 110.2 and 110.3. The sieves 110.1, 110.2 and 110.3 of the sieve assembly comprise a plurality of spacings or apertures 120 through which a component of the crop (e.g. a seed component) can fall, thereby separating the component from the remaining part of the harvested crop. The separation of the components takes place during a transport (indicated by the arrows 130) of the harvested crop along a top surface of the sieves. In the embodiment as shown, the separated component which has fallen through the sieve is transported towards an auger 140 (as indicated by the arrow 145) which can e.g. transport the component towards a grain tank. The remainder of the harvested crop (MOG, chaff) is transported towards a second auger 150 (as indicated by the arrow 155).

The embodiment as shown in FIG. 1 further comprises a fan 160 configured to provide an air flow upward through the sieves of the sieve assembly 110. Arrows 165 schematically indicate the air flow through the sieves as can be generated by the fan. An upward air flow through the sieve or sieves of the sieve assembly promotes the separation of the different components of the flow of harvested crop. Depending on the component to be separated, an optimal velocity of the flow of air through the sieve can be determined FIG. 1 further schematically shows a rotatable output shaft 175 of a drive assembly for driving the cleaning system 100. In accordance with the present invention, the rotatable output shaft 170 is part of a variable speed drive assembly, further including a transmission (176, 177, 178) to convert an angular movement of the rotatable output shaft 175 to a reciprocating movement of the cleaner assembly or assemblies. Such a conversion may e.g. be obtained by means of a transmission including an eccentric device 176,177 and an arm 178 connecting the eccentric device 176,177 to the one or more cleaner assemblies. The eccentric device as schematically shown comprises, a circular element 176 which is eccentrically connected at a shaft connection point to the rotatable drive shaft 175 to rotate with the rotatable drive shaft. The transmission further comprises an annular member 177. This annular member 177 extends around the circular element 176 and is pivotable around said circular element 176 for example by means of a bearing the extends between the circular element 176 and the annular member 71. The transmission as shown further comprises an arm 178. The arm 178 has a first end that is fixedly connected to the annular member 177. A second end is in connection with one of the cleaner assemblies via pivot 180. In the embodiment as shown, sieves 110.1, 110.2 and grain pan 105.2 may e.g. be mounted to a common frame (not shown) which is driven via pivot 180. The assembly of sieves 110.1, 110.2 and grain pan 105.2 may thus form a first cleaner assembly of the cleaning system. Grain pan 105.1 and sieve 110.3 may e.g. be mounted to separate, different frames thus forming a second respectively third cleaner assembly. These second and third assembly may be driven in a similar manner as the first cleaner assembly (110.1, 110.2, 105.2), i.e. by means of arms (not shown) connecting the eccentric device with the assemblies. Alternatively (as shown in more detail in FIG. 2), they may be driven by means of connecting arms (not shown) connecting the first and second cleaner assembly and connecting the first and third cleaner assembly (see FIG. 2).

As schematically shown, the transmission enables the conversion for an angular movement to a reciprocating movement of the cleaner assembly or assemblies. Such a reciprocating movement can be described as a circular or elliptical movement comprising a first portion whereby the cleaner assembly is moved forwards and downwards and a second portion whereby the cleaner assembly is moved backwards and upwards. Such a movement enables a flow of harvested and threshed crop which is supplied to the one or more cleaner assemblies (e.g. to the grain pan 105.1), to be moved or propagated towards the back end. In the embodiment as shown, the flow of crop may subsequently be received by the cleaner assembly comprising the sieves 110.1, 110.2 and grain pan 105.2 and subsequently by the cleaner assembly comprising the sieve 110.3. In accordance with the present invention, the rotatable output shaft 175 is part of a variable speed drive assembly configured to drive the one or more cleaner assemblies at a variable speed. As such, in accordance with the present invention, the angular velocity of the rotatable output shaft 175 can be adjusted to take into account the operating conditions of the combine harvester. In order to render the angular velocity of the rotatable output shaft adjustable or controllable, various options exist. In an embodiment, the rotary drive may e.g. be a dedicated variable speed drive for driving the cleaning system. In order to adjust the angular velocity of an output shaft of such a drive, a variator, a gear box or a variable transmission such as a CVT (continuous variable transmission) or IVT (infinitely variable transmission) may be applied. A variator or a CVT may be described as a mechanical power transmission device of which a gear ratio may the changed continuously, rather than in steps. In order to realise such continuously variable transmission, use can e.g. be made of a pair of pulleys (e.g. V-belt pulleys) having a variable diameter combined with a V-belt running between them. In such arrangement, the distance between the pair of sheaves of each pulley can be adjusted, thereby changing the gear ratio. In particular, the gear ratio is changed by moving the two sheaves of one pulley closer together and the two sheaves of the other pulley further apart. Due to the V-shaped cross section of the belt, this causes the belt to ride higher on one pulley and lower on the other. Doing this changes the effective diameters of the pulleys, which in turn changes the overall gear ratio. In such arrangement, the distance between the pulleys does not change, and neither does the length of the belt, in case both pulleys are adjusted.

In accordance with the present invention, the angular speed of the output shaft can be controlled, i.e. adjusted. The variable speed drive assembly therefore comprises a control unit 190 configured to control an angular velocity of the rotatable output shaft 175 based on an input signal 192 received at an input terminal 194 of the control unit 190. Such a control unit 190 may e.g. include a microcontroller or microprocessor or the like. The input signal 192 as received by the control unit 190 (via the input terminal 194) may e.g. be generated by a user interface available in a cabin of the combine harvester, enabling an operator of the harvester to provide the input signal to the control unit.

Alternatively, the input signal for the control unit may be based on a sensor signal provided by a sensor 196.

As an example, the combine harvester according to the present invention may comprise a sensor 196 for sensing an inclination of the combine harvester, the sensor being configured to provide a signal representative of the inclination as an input signal 192 to the control unit 190. The sensor 196 may as an alternative or in addition include a GPS sensor e.g. providing a position signal and a signal representing the driving direction of the harvester to the control unit 190. In such arrangement, the control unit 190 may be configured to determine an inclination of the combine harvester based on the signals received. Alternatively, the GPS sensor may be configured to determine a signal representative of the inclination based on the position and driving direction and provide the signal to the input terminal 192 of the control unit 190.

In accordance with the present invention, communication from the sensor 196 to the control unit 190 or from a user interface to the control unit 190 may be realized by wireless communication or wired types of communication.

Typically, a combine harvester comprises a central drive having a input shaft (driven by the engine of the harvester), whereby the input shaft is used to drive (by means of variable or fixed transmissions) one or more rotatable shafts for e.g. driving a threshing system, a transport system and the cleaning system. Typically, the input shaft has a substantially constant angular velocity during operation. In such arrangement, a rotary drive having a rotary output shaft with an adjustable angular velocity may be obtained by combining the central drive of the combine harvester with a variable transmission such as a variator or a CVT (continuous variable transmission) or IVT (infinitely variable transmission).

In an embodiment of the present invention, the angular velocity of the rotatable output shaft is adjusted based on a determined inclination of the combine harvester. It has been observed by the inventors that the effectiveness of the cleaning system 100, i.e. the effectiveness of the separation process of seeds and by-products by the one or more cleaner assemblies, may depend on the operating conditions of the harvester, in particular the inclination of the harvester. It has e.g. been noticed that, in case the combine harvester moves up-hill, the flow of seeds and by-products that need to be separated (indicated by the arrow 130 in FIG. 1) may propagate too fast towards the end of the sieve or sieves, thereby adversely affecting the yield of the separation process. Similarly, in case the combine harvester moves downhill, the flow of seeds and by-products that need to be separated may propagate too slow towards the end of the sieve. As a result, a varying capacity (i.e. the amount of harvested and threshed crop processed by the cleaning system per unit of time) may be noticed. Such a varying capacity may adversely affect the removal and transport of the clean grain towards an on-board grain tank by a transport system (e.g. an auger based transport system as indicated by augers 140 and 150), because this transport system is typically dimensioned to handle a particular capacity.

By means of the variable speed drive system as applied in the combine harvester according to the present invention, the operating speed of the cleaning system can be adjusted such that the capacity of the cleaning system, i.e. the amount of cleaned crop, may remain substantially constant.

In order to realize this, the operating speed of the cleaning system, in particular the reciprocating cleaner movement needs to be reduced in case the harvester drives up-hill and needs to be increased in case the harvester drives down-hill.

In an embodiment, the cleaning system is provided with one or more load sensors 198 configured to provide a signal representative of the capacity or load, i.e. the amount of harvested and threshed crop that is processed, of the cleaning system. Such a load sensor can e.g. be a pressure sensor or a grain fall through sensor mounted below the sieve. By monitoring the pressure that is build up, e.g. below a sieve, an indication can be obtained of the amount of crop that is processed by the sieve.

In an embodiment, the load sensor comprises an array of sensors arranged along the sieve.

In an embodiment, the load sensor signal may be provided to the control unit 190 as a feedback of the capacity of the cleaning system.

In an embodiment, the control unit 190 can be configured to control the angular velocity speed of the rotatable output shaft 175 based on such a load sensor signal. In such embodiment, the input signal 192 received at an input terminal 194 of the control unit 190 may thus comprise, in addition or as an alternative, a load sensor signal representing the actual capacity or load of the cleaning system. Such a load sensor signal may thus be considered a feedback signal and may be used by the control unit as a check or verification of the adjustment made to the angular velocity of the output shaft 175.

In an embodiment, an angular velocity of the fan 160 may also be adjusted when the angular velocity of the output shaft 175 is adjusted. In an embodiment, the fan 160 may be driven by the same variable speed drive assembly used for driving the cleaning system 200. In such embodiment, the fan 160 may e.g. be driven by the rotatable output shaft 175, e.g. by means of a belt or belt-type connection.

Figure 2:
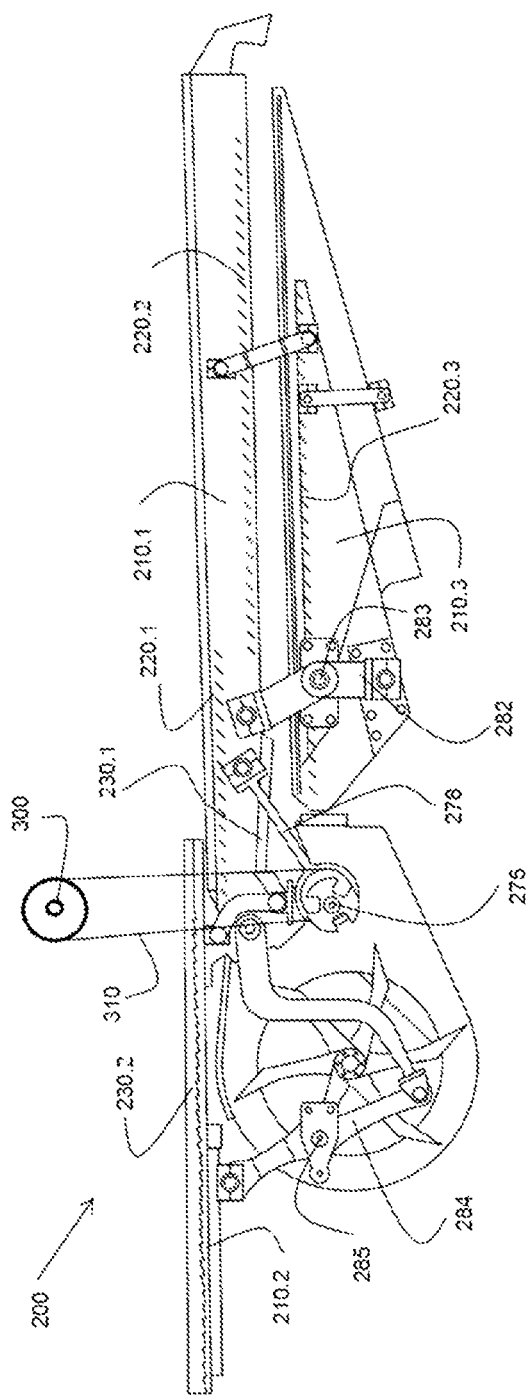
FIG. 2 depicts a cleaning system including three cleaner assemblies as can be applied in a combine harvester according to the present invention.

FIG. 2 schematically shows a more detailed side view of a cleaning system 200 as can be applied in a combine harvester according to the present invention. The cleaning system comprises three cleaner assemblies 210.1, 210.2 and 210.3 each comprising one or more sieves or grain pans.

As can be seen, cleaner assembly 210.1 comprises first and second sieves 220.1, 220.2 and a first grain pan 230.1, cleaner assembly 210.2 comprises a third sieve 220.3, cleaner assembly 210.3 comprises a second grain pan 230.2. The embodiment as shown further comprise a drive assembly including a rotatable output shaft 275 and transmission 278 for converting an angular movement of the rotatable output shaft 275 to a reciprocating movement of the cleaning system. In the embodiment as shown, the transmission 278 acts on the first cleaner assembly 210.1, while the second and third cleaner assemblies are driven by means of pivotable arms 282, 284 connecting the second and third cleaner assemblies to the first cleaner assembly. Pivotable arms 282 and 284 may pivot about fixed pivot points 283 and 285 which may be fixed to a frame of the combine harvester (not shown). FIG. 2 further shows a central drive having a rotatable input shaft 300, the input shaft during use e.g. being driven by the engine of the combine harvester, at a substantially constant speed. A variable transmission 310 is further shown between the input shaft 300 and the output shaft 275, the variable transmission being configured to provide in a variable angular velocity of the rotatable output shaft 275. The variable transmission 310 may e.g. comprise a variator or CVT as discussed above. With respect to a variable transmission comprising a CVT, reference may e.g. be made to EP1375977 describing a variable speed drive arrangement for a threshing system.

The variable transmission 310 as schematically shown may further be controlled by a control unit receiving an input signal (as discussed above) representing an operating condition such as an inclination of the combine harvester.

By applying a variable angular velocity to the rotatable output shaft driving the cleaning system, the variation being controlled depending on the operating conditions, the capacity or yield of the cleaning system can be maintained substantially constant. As such, a transport system of the harvester, e.g. configured to transport clean grain to an on-board tank, may receive a substantially constant flow of clean grain to be transported. As such, an operating speed of the transport system can be maintained substantially constant. In order to realize this, in an embodiment of the present invention, the transport system (e.g. including augers 140 and 150 as shown in FIG. 1) may be driven by means of a fixed transmission (i.e. a transmission having a fixed gear ratio), e.g. a belt transmission having two fixed pulleys, e.g. connecting the input shaft 300 with a shaft of the transport system (not shown). As such, during use, the transport system or transport assembly of the combine harvester according th the embodiment of the invention may operate at a substantially constant speed, irrespective of the angular velocity of the rotatable output shaft 275.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

The invention claimed is:

1. A combine harvester comprising:
 a cleaning system comprising at least one cleaner assembly to clean harvested and threshed crop, the at least one cleaner assembly comprising one or more sieves;
 a fan for providing an upward air flow through the one or more sieves of the at least one cleaner assembly;
 a drive assembly connected to the cleaning system and configured to drive the cleaning system, thereby driving the at least one cleaner assembly to perform a reciprocating cleaner movement, the drive assembly comprising a variable speed drive assembly comprising:
  a rotary drive comprising a rotatable output shaft for driving the one or more sieves of the at least one cleaner assembly of the cleaning system and the fan;
  a transmission configured to connect the rotatable output shaft to the at least one cleaner assembly of the cleaning system, the transmission further configured to convert an angular movement of the rotatable output shaft to the reciprocating cleaner movement; and
  a control unit configured to control an angular velocity of the rotatable output shaft based on an input signal, which the input signal represents an inclination of the combine harvester, received by the control unit, the control unit further configured to reduce the angular velocity of the rotatable output shaft when the inclination is positive and to increase the angular velocity of the rotatable output shaft when the inclination is negative, wherein an angular velocity of the fan is controlled by the control unit, proportional to the angular velocity of the rotatable output shaft; and
 a transport system for transporting the cleaned harvested and threshed crop to a storage tank, the transport system driven at a substantially constant speed.

2. The combine harvester according to claim 1, wherein the rotary drive further comprises a rotatable input shaft and a variable transmission, the variable transmission connecting the rotatable input shaft and the rotatable output shaft, and wherein the control unit is further configured to control a gear ratio of the variable transmission based on the input signal, thereby controlling the angular velocity of the rotatable output shaft.

3. The combine harvester according to claim 2, wherein the rotatable input shaft is configured to operate at a substantially constant angular velocity during use, the rotary drive further comprising a fixed transmission connecting the rotatable input shaft and the transport system, the fixed transmission having a fixed gear ratio for driving the transport system at the substantially constant speed, irrespective of the angular velocity of the rotatable output shaft.

4. The combine harvester according to claim 1, wherein the transmission comprises an eccentric device for converting the angular movement to the reciprocating cleaner movement.

5. The combine harvester according to claim 1, further comprising an inclination sensor for generating the input signal.

6. The combine harvester according to claim 1, further comprising a load sensor configured to provide a load sensor signal representing a load of the cleaning system.

7. The combine harvester according to claim 6, wherein the input signal further comprises the load sensor signal, and wherein the control unit is configured to control the angular velocity of the rotatable output shaft based on the load sensor signal.

8. The combine harvester according to claim 6, wherein the load sensor comprises at least one of a pressure sensor and a grain fall through sensor.

9. The combine harvester according to claim 1, wherein the at least one cleaner assembly further comprises a grain pan.

10. The combine harvester according to claim 1, wherein the at least one cleaner assembly further comprises a grain pan, and wherein the transmission is configured to convert the angular movement of the rotatable output shaft to a reciprocating sieve movement and a reciprocating grain pan movement.

11. The combine harvester according to claim 1, further comprising a threshing system configured to thresh a flow of harvested crop and provide the harvested and threshed crop to the cleaning system.

* * * * *